United States Patent [19]
Holman

[11] Patent Number: 5,980,533
[45] Date of Patent: Nov. 9, 1999

[54] STENT DELIVERY SYSTEM

[75] Inventor: Thomas J. Holman, Minneapolis, Minn.

[73] Assignee: Scimed Life Systems, Inc., Maple Grove, Minn.

[21] Appl. No.: 09/094,123

[22] Filed: Jun. 9, 1998

[51] Int. Cl.⁶ ..................................................... A61F 11/00
[52] U.S. Cl. ........................................... 606/108; 606/191
[58] Field of Search ..................................... 606/108, 191, 606/159

[56] References Cited

U.S. PATENT DOCUMENTS

| | | | |
|---|---|---|---|
| 4,762,128 | 8/1988 | Rosenbluth | 604/96 |
| 5,158,548 | 10/1992 | Lau et al. | 604/96 |
| 5,242,399 | 9/1993 | Lau et al. | 604/104 |
| 5,534,007 | 7/1996 | St. Germain et al. | 606/108 |

FOREIGN PATENT DOCUMENTS

98/12988  4/1998  WIPO .

*Primary Examiner*—Michael Buiz
*Assistant Examiner*—Vy Q. Bui
*Attorney, Agent, or Firm*—Vidas, Arrett & Steinkraus, P.A.

[57] ABSTRACT

A stent delivery catheter comprising an elongated catheter shaft having a mounting region at the distal end for mounting a stent thereon. The elongated catheter shaft has a lumen therein for receiving an inner shaft. An inner shaft is movably carried within the lumen of the elongated catheter shaft. Extending distally from the distal end of the inner shaft is a tip. A retractable sheath extends proximally from the proximal end of the tip. The sheath, in an unretracted position covers the mounting region of the elongated catheter shaft. In use, once the catheter is in the desired bodily location, the inner shaft is moved in a distal direction relative to the elongated catheter shaft which causes the retractable sheath to be moved in a distal direction relative to the mounting region thereby exposing the stent for delivery.

14 Claims, 3 Drawing Sheets

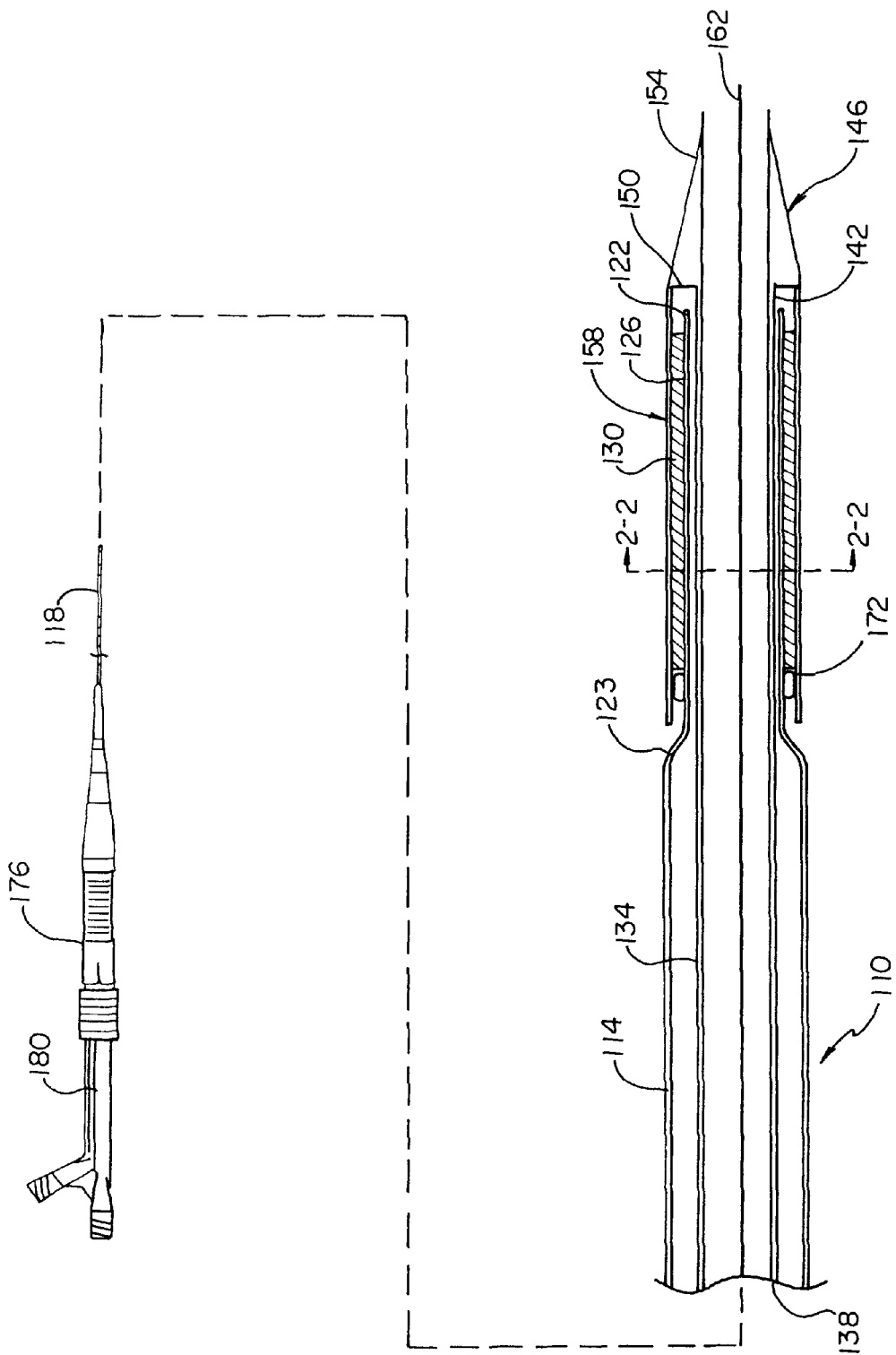

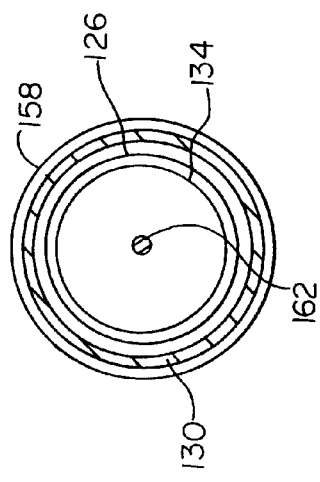
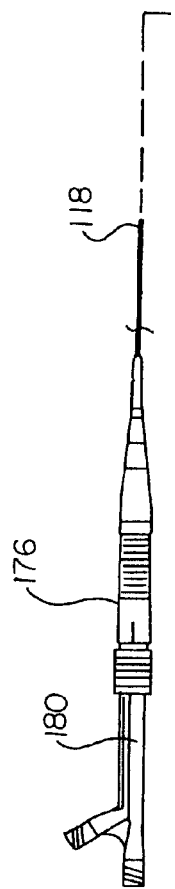
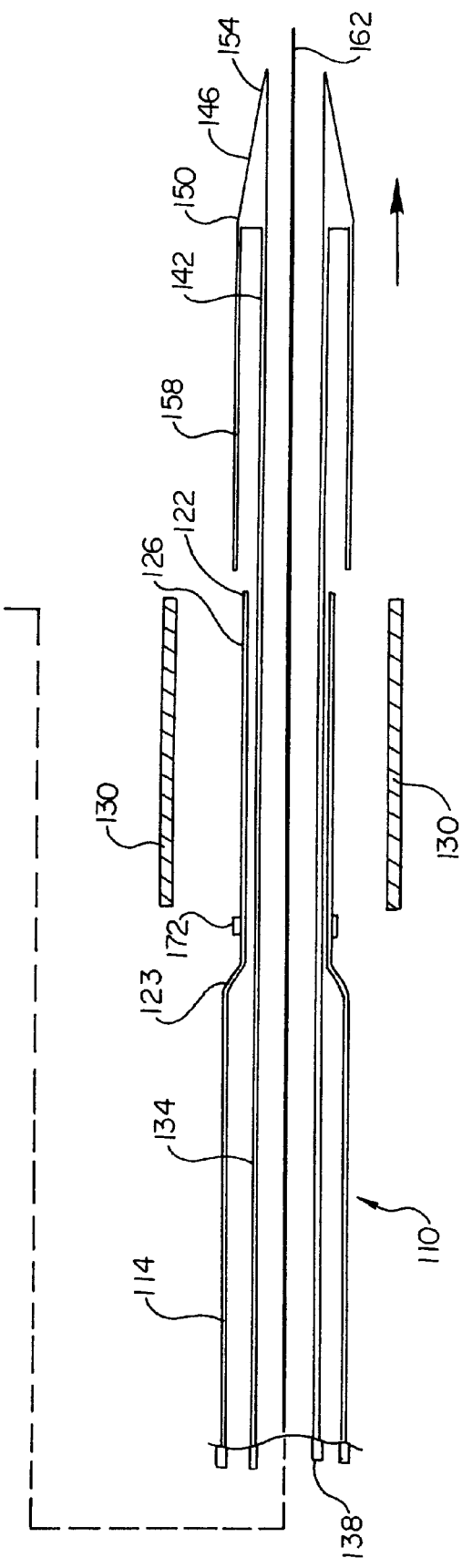

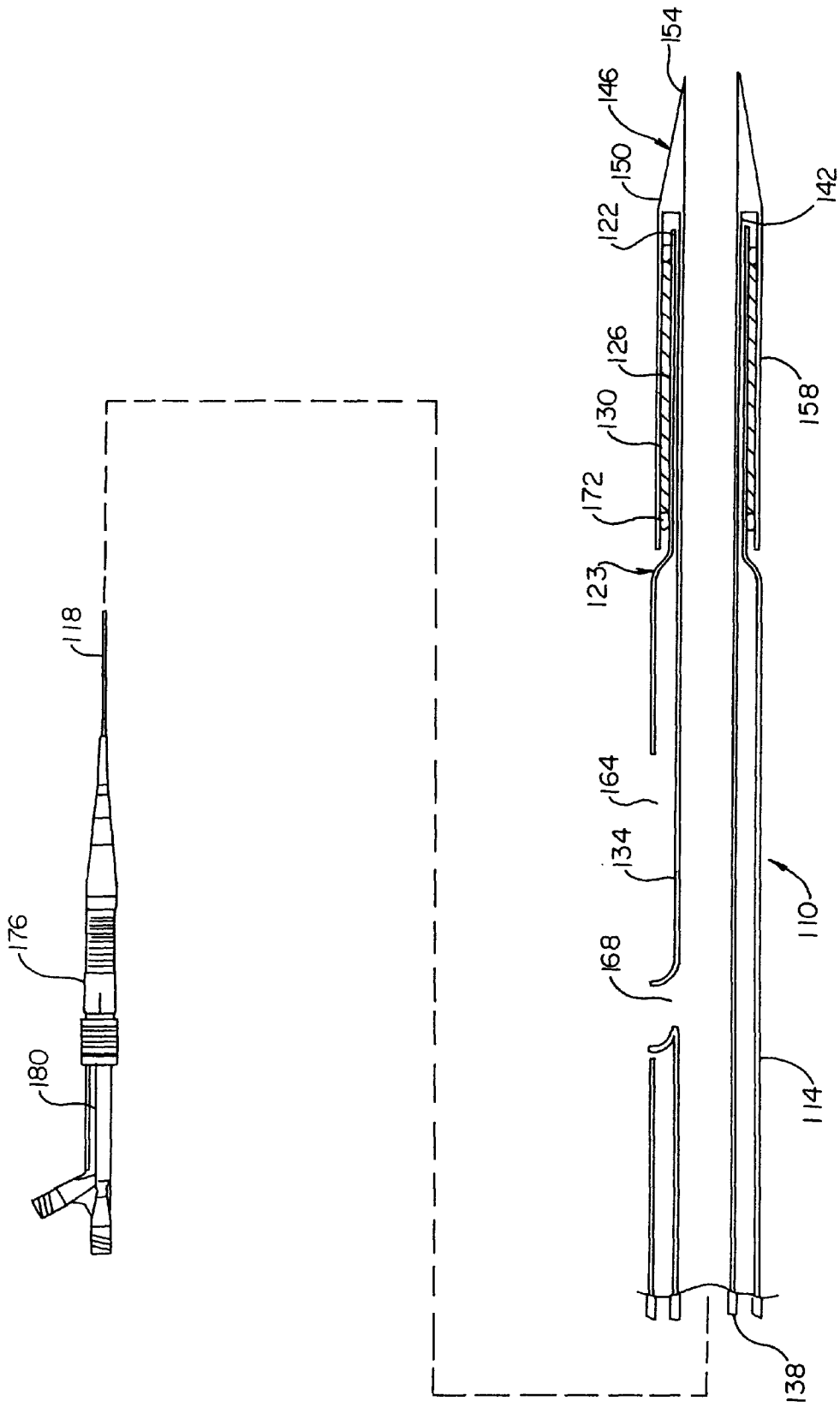

STENT DELIVERY SYSTEM

BACKGROUND OF THE INVENTION

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter has a guide wire lumen which is as long as the catheter. Another type of catheter, a rapid exchange catheter wherein the guide wire lumen is substantially shorter than the catheter may be used. Alternatively, a fixed wire balloon may be used. This device features a guide wire which is affixed to the catheter and cannot be removed.

To help prevent arterial closure, repair dissection, or prevent or lower restenosis, a physician can implant an intravascular prosthesis, or a stent, for maintaining vascular patency inside the artery at the lesion. In particular, a stent is a prosthesis which is generally tubular and which is expanded radially in a vessel or lumen to maintain its patency. Stents are widely used in body vessels, body canals, ducts or other body lumens. The stent may either be a balloon or otherwise mechanically expandable stent or a self-expanding stent.

For the former type, the stent is often delivered on a balloon and the balloon is used to expand the stent exerting radial force on the constricted portion of the body lumen to re-establish patency. A common material for balloon expandable stents is stainless steel.

For the latter type, the self-expanding stents may be made of shape memory materials such as nitinol or constructed of regular metals but of a design which exhibits self expansion characteristics. Self-expanding stents are typically constrained onto the delivery catheter by means of a retractable sheath covering the stent. The self-expanding stent expands from a compressed delivery position to its original diameter when released from the delivery device, exerting radial force on the constricted portion of the body lumen to re-establish patency. One common self-expanding stent is manufactured of Nitinol, a nickel-titanium shape memory alloy, which can be formed and annealed, deformed at a low temperature, and recalled to its original shape with heating, such as when deployed at body temperature in the body.

To date, several different types of catheters with retractable sheaths have been disclosed. In one type of catheter, the sheath retracts in a proximal direction. Examples of such catheters are disclosed in WO 98/12988 as well as in U.S. Pat. No. 5,534,007 to St. Germain, both of which are incorporated herein in their entirety by reference. In another type of catheter, as described in U.S. Pat. No. 5,158,548 to Lau and U.S. Pat. No. 5,242,399 to Lau, the sheath is attached to a guidewire and moved in a distal direction to release a stent for delivery. As such, the guidewire cannot be operated independently of the sheath.

The present invention is directed to a catheter having a sheath which is retractable in the distal direction and which is suitable for use as a rapid exchange catheter, an over-the-wire catheter or a fixed wire catheter.

SUMMARY OF THE INVENTION

The present invention pertains to a medical treatment device delivery catheter. The catheter comprises an elongated catheter shaft having a mounting region at the distal end for mounting a medical treatment device thereon. The elongated catheter shaft has a lumen therein for receiving an inner shaft. An inner shaft is movably carried within the lumen of the elongated catheter shaft. Extending distally from the distal end of the inner shaft is a tip. A retractable sheath extends proximally from the proximal end of the tip. The sheath is movable, desirably slidable, from an unretracted position in which the sheath covers the mounting region of the elongated catheter shaft and any medical device mounted thereon, to a fully retracted position in which the mounting region and any medical device thereon is fully exposed for delivery. The sheath is retracted distally by moving, desirably sliding, the inner shaft in a distal direction relative to the elongated catheter shaft. This, in turn, moves the tip in a distal direction which, similarly, causes the retractable sheath to be moved in a distal direction relative to the mounting region, thereby delivering the medical treatment device.

A manifold, including means for moving the inner shaft through the elongated catheter shaft, is provided at the proximal end of the medical treatment device delivery catheter. Desirably, the manifold will be constructed and arranged so as to allow for a relative sliding motion between the inner shaft and the elongated catheter shaft.

In one embodiment, the medical device is an expandable stent. While either balloon or otherwise mechanically expandable stents may be used in the practice of the invention, preferably a self-expanding stent will be used.

The inventive medical treatment device delivery catheter may be used in connection with over the wire (OTW), single operator exchange (SOE)/rapid exchange (RX) or fixed wire catheter configurations.

The present invention also pertains to a method of delivering an expandable stent to a selected location within a bodily lumen. An expandable stent is mounted on the mounting region of a medical device delivery catheter such as the one described above. The retractable sheath is disposed over the expandable stent. The catheter is next inserted into a bodily lumen and advanced until the stent bearing region of the catheter is disposed in a desired location within a bodily lumen. The inner shaft is advanced distally relative to the elongated catheter shaft thereby causing the tip to move in a distal direction as well. This, in turn, causes the sheath to be advanced distally relative to the elongated catheter shaft and stent so as to expose the expandable stent. The expandable stent is then expanded or allowed to expand, depending on whether the stent is mechanically expandable, such as by balloon, or whether the stent is self-expanding. Finally, the stent delivery catheter is removed from the bodily lumen, the stent having been placed in the desired location.

BRIEF DESCRIPTION OF THE FIGURES

FIG. 1 shows a partial cross-section side elevational view of an over-the-wire embodiment of the inventive catheter.

FIG. 2 shows a transverse cross-sectional view of the inventive catheter along lines 2—2 as shown in FIG. 1.

FIG. 3 shows a partial cross-section side elevational view of an over-the-wire embodiment of the inventive catheter with the retractable sheath fully retracted.

FIG. 4 shows a partial cross-section side elevational view of a single operator exchange (SOE)/rapid exchange (RX) embodiment of the inventive catheter.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

FIGS. 1–3 illustrate a treatment device delivery system which embodies the features of the invention. For illustrative purposes, the distal end of the delivery system has been enlarged in FIGS. 1, 3 and 4. The treatment device delivery system, shown generally at 110 includes an elongated catheter shaft 114 having a proximal end 118 and a distal end 122. Elongated catheter shaft 114 desirably has a tapered region 123, with distal end 122 of the elongated catheter shaft 114 having a smaller outer diameter than proximal end 118. At the distal end 122 of the elongated catheter shaft 114 is a mounting region 126 for mounting a treatment device 130 thereon. Elongated catheter shaft 114 has a lumen therein for receiving an inner shaft.

The treatment device delivery system further comprises an inner shaft 134 movably carried within the lumen of the elongated catheter shaft 114. Inner shaft 134 has a proximal end 138 and a distal end 142.

Tip 146 extends distally from distal end 142 of inner shaft 134. Tip 146 has a proximal end 150 and a distal end 154. Tip 146 may be secured to inner shaft 134 by a suitable means such as an adhesive or may be formed integrally with the inner shaft.

Extending proximally from proximal end 150 of tip 146 is a retractable sheath 158. In the unretracted position, as shown in FIGS. 1 and 4, retractable sheath 158 covers mounting region 126 of elongated catheter shaft 114. Retractable sheath 158 is generally cylindrical in shape and is constructed and arranged to fit over treatment device 130 when the retractable sheath is not retracted. In embodiments in which elongated catheter 114 has a tapered region 123, retractable sheath 158 has an outer diameter substantially similar to that of elongated catheter shaft proximal to the tapered region. This results in the catheter presenting a substantially uniform profile.

While retractable sheath 158 may be secured to tip 146 by suitable means such as an adhesive, the retractable sheath may also be formed integrally with the tip.

Desirably, as shown in FIG. 1, treatment device 130 is a stent, although the invention contemplates other treatment devices as well such as grafts, collars, and implantable filters. More desirably, treatment device 130 is a self-expanding stent. While any self-expanding stent may be used, a preferred self-expanding stent for use with the present invention is the radius stent, described in U.S. patent application Ser. No. 08/511076 filed Aug. 3, 1995 and incorporated herein by reference. Of course, balloon or other mechanically expandable stents may be used as well in the practice of the present invention. In the case of a balloon mounted stent, the catheter further comprises a balloon carried on the mounting region and at least partially underneath the stent as well as an additional shaft to provide an inflation lumen for the balloon. A suitable balloon expandable stent is the NIR stent.

In an application where a self-expanding stent is used, retractable sheath 158 will be constructed and arranged to fit snugly over the stent so as to maintain the stent in its unexpanded state.

A manifold 176, including means to move the inner shaft through the elongated catheter shaft, is provided at the proximal end 118 of the medical treatment device delivery catheter. Desirably, the manifold will be constructed and arranged so as to allow for a relative sliding motion between the inner shaft and the elongated catheter shaft. To that end, a suitable slide mechanism 180, as is known in the art, may be employed.

The inventive catheter may be used in connection with over the wire (OTW), single operator exchange (SOE)/rapid exchange (RX) or fixed wire catheter configurations. As shown in FIG. 1, an over the wire embodiment of the inventive catheter, catheter 110 may be advanced over guidewire 162 carried within inner shaft 134 and extending out of the distal end of the catheter through tip 146. Note that in this embodiment, guidewire 162 is carried within the entire length of the catheter.

In the single operator exchange (SOE)/rapid exchange (RX) embodiment shown in FIG. 4, elongated catheter shaft 114 has an opening 164 therein to allow for entry of a guidewire (not shown) into inner shaft 134. Similarly, inner shaft 134 has an inlet port 168 therein to allow for entry of the guidewire into inner shaft 134. In the SOE/RX embodiment, the guidewire runs within the catheter for only a short length, as seen in FIG. 4.

Optionally, the inventive catheter may further comprise one or more marker bands 172 mounted on elongated catheter shaft 114 in the mounting region 126, coaxially with the elongated catheter shaft. The inventive catheter may further optionally comprise one or more bumpers (not shown) as are known in the art, mounted on the elongated catheter shaft in the mounting region.

A transverse cross-section of the embodiment of FIG. 1 is shown in FIG. 2. Retractable sheath 158, stent 130, elongated catheter shaft 126 and inner shaft 134 are concentrically arranged about the longitudinal axis of the catheter. In the center is guidewire 162.

In use, as shown in FIG. 3, inner shaft 134 is moved in a distal direction relative to elongated catheter shaft 114 to cause retractable sheath 158 to be moved in a distal direction relative to mounting region 126, as indicated by the arrow. Once retractable sheath 158 has been completely removed from mounting region 126, as shown in FIG. 3, treatment device 130 may be delivered. As seen in FIG. 3, the treatment device, a stent 130, has been expanded.

Conventional materials, as are known in the art, may be used in the construction of the inventive treatment device delivery catheter. Similarly, convention methods of manufacture, as are known in the art, may be employed in manufacturing the inventive catheters. The elongated catheter shaft may be formed of a single or multilayer extrusion, optionally with tension wires therein. Suitable polymers for the extrusion include polyethylene, polyester and polyimide and other thermoplastic polymers along with thermoset polymers and silicones. The inner tube may be similarly formed. The tip may be bonded to the inner shaft and the retractable sheath may be bonded to the tip by suitable means including the use of methacrylic based adhesives or acrylonitrile based adhesives.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A medical treatment device delivery catheter comprising:

an elongated catheter shaft having a proximal end and a distal end, the elongated catheter shaft having a mounting region at the distal end for mounting a medical treatment device thereon, the elongated catheter shaft having a lumen therein;

an inner shaft movably carried within the lumen of the elongated catheter shaft, the inner shaft having a proximal end and a distal end, the inner shaft having a lumen therein;

a tip extending distally from the distal end of the inner shaft, the tip having proximal and distal ends;

a retractable sheath extending proximally from the proximal end of the tip, the sheath covering the mounting region of the elongated catheter shaft;

wherein the inner shaft is moved in a distal direction relative to the elongated catheter shaft to cause the retractable sheath to be moved in a distal direction relative to the mounting region to deliver the medical treatment device.

2. The medical treatment device delivery catheter of claim 1 wherein the medical treatment device is a stent and the retractable sheath may be retracted to expose the stent to expand from an initial unexpanded state to a final expanded state.

3. The medical treatment device delivery catheter of claim 1 wherein the catheter shaft has a taper therein, the outer diameter of the distal end of the elongated catheter shaft smaller than the outer diameter of the proximal end of the elongated catheter shaft.

4. The medical treatment device delivery catheter of claim 3 wherein the outer diameter of the retractable sheath is substantially the same as the outer diameter of the elongated catheter shaft.

5. The medical treatment device delivery catheter of claim 2 wherein the stent is self expandable.

6. The medical treatment device delivery catheter of claim 2 further comprising one or more marker bands, the one or more marker bands mounted on the elongated catheter shaft in the mounting region.

7. The medical treatment device delivery catheter of claim 1 wherein the catheter is an over the wire catheter.

8. The medical treatment device delivery catheter of claim 1 wherein the catheter is a fixed wire catheter.

9. The medical treatment device delivery catheter of claim 1 wherein the catheter is a rapid exchange catheter.

10. The catheter of claim 1 further comprising a guidewire carried within the inner shaft.

11. A stent delivery catheter having a longitudinal axis, the catheter comprising:

an elongated catheter shaft having a proximal end and a distal end, the elongated catheter shaft having a mounting region at the distal end for mounting a stent thereon, the elongated catheter shaft having a lumen therein;

an inner shaft slidably carried within the lumen of the elongated catheter shaft, the inner shaft having a proximal end and a distal end, the inner shaft having a lumen therein, the inner shaft and elongated catheter shaft disposed coaxially about the longitudinal axis;

a tip extending distally from the distal end of the inner shaft, the tip having proximal and distal ends;

a tubular retractable sheath extending proximally from the proximal end of the tip, the sheath covering the mounting region of the elongated catheter shaft, the sheath and the elongated catheter shaft coaxially disposed about the longitudinal axis;

wherein the inner shaft is moved in a distal direction relative to the elongated catheter shaft to cause the retractable sheath to be moved in a distal direction relative to the mounting region to deliver the stent.

12. The catheter of claim 11 further comprising a guidewire carried within the inner shaft.

13. A method of delivering an expandable stent to a selected location within a bodily lumen comprising:

a) providing a stent delivery catheter comprising an elongated catheter shaft, an inner shaft movably carried therein, the inner shaft having a lumen therein, a tip extending from the distal end of the inner shaft, the elongated catheter further having a mounting region at the distal end constructed and arranged so as to be able to carry an expandable stent thereon, the catheter further comprising a sheath extending from the proximal end of the tip, the sheath constructed and arranged so as to cover a stent mounted on the elongated catheter shaft;

b) mounting an expandable stent on the mounting region;

c) disposing the sheath over the expandable stent mounted on the mounting region;

d) advancing the stent delivery catheter through a bodily lumen until the stent is disposed in a desired location within a bodily lumen;

e) advancing the inner shaft distally relative to the elongated catheter shaft thereby causing the sheath to be advanced distally relative to the elongated catheter shaft and stent so as to expose the expandable stent;

f) expanding the expandable stent;

g) removing the stent delivery catheter from the bodily lumen.

14. The method of claim 13 wherein the catheter further comprises a guidewire carried within the inner shaft.

* * * * *